US009836560B1

(12) United States Patent
Bramson et al.

(10) Patent No.: US 9,836,560 B1
(45) Date of Patent: *Dec. 5, 2017

(54) COMPUTER SIMULATION OF PROBIT METHOD OF CUMULATIVE DISTRIBUTION FUNCTION DETERMINATION OF ENERGETIC SENSITIVITY

(71) Applicant: The United States of America as Represented by the Secretary of the Navy, Washington, DC (US)

(72) Inventors: Michael D. Bramson, Ridgecrest, CA (US); Tom J. Schilling, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 479 days.

This patent is subject to a terminal disclaimer.

(21) Appl. No.: 14/601,456

(22) Filed: Jan. 21, 2015

Related U.S. Application Data

(60) Provisional application No. 61/935,539, filed on Feb. 4, 2014.

(51) Int. Cl.
G06F 7/60 (2006.01)
G06F 17/10 (2006.01)
G06F 17/50 (2006.01)

(52) U.S. Cl.
CPC .......... *G06F 17/5009* (2013.01); *G06F 17/10* (2013.01)

(58) Field of Classification Search
None
See application file for complete search history.

(56) References Cited

U.S. PATENT DOCUMENTS

2003/0004679 A1* 1/2003 Tryon, III ............. G06F 11/008
702/182
2004/0130702 A1* 7/2004 Jupp .................... G06K 9/0063
356/5.01

OTHER PUBLICATIONS

Petersen, E.L., et al., "Rate Prediction for Single Event Effects", Dec. 1992, IEEE Transactions on Nuclear Science, vol. 39, No. 6, IEEE.*

* cited by examiner

*Primary Examiner* — Cedric D Johnson
(74) *Attorney, Agent, or Firm* — James M. Saunders

(57) ABSTRACT

Embodiments of the invention simulate the actual shape of a cumulative distribution function (CDF) that describes the energetic sensitivity of an energetic composition. Sensitivity tests and historical data are input into an electronic processor. Response data points are obtained through electronic analysis and a best fit curve is produced through the response points and produced as output in a tangible medium.

18 Claims, 9 Drawing Sheets

COMPUTER SIMULATION OF PROBIT METHOD OF CUMULATIVE DISTRIBUTION FUNCTION DETERMINATION OF ENERGETIC SENSITIVITY

CROSS-REFERENCE TO RELATED APPLICATIONS

This is a non-provisional application, claiming the benefit of parent provisional application No. 61/935,539 filed on Feb. 4, 2014, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to the determination of the sensitivity of energetic materials to explosive shock.

Figure 1A:
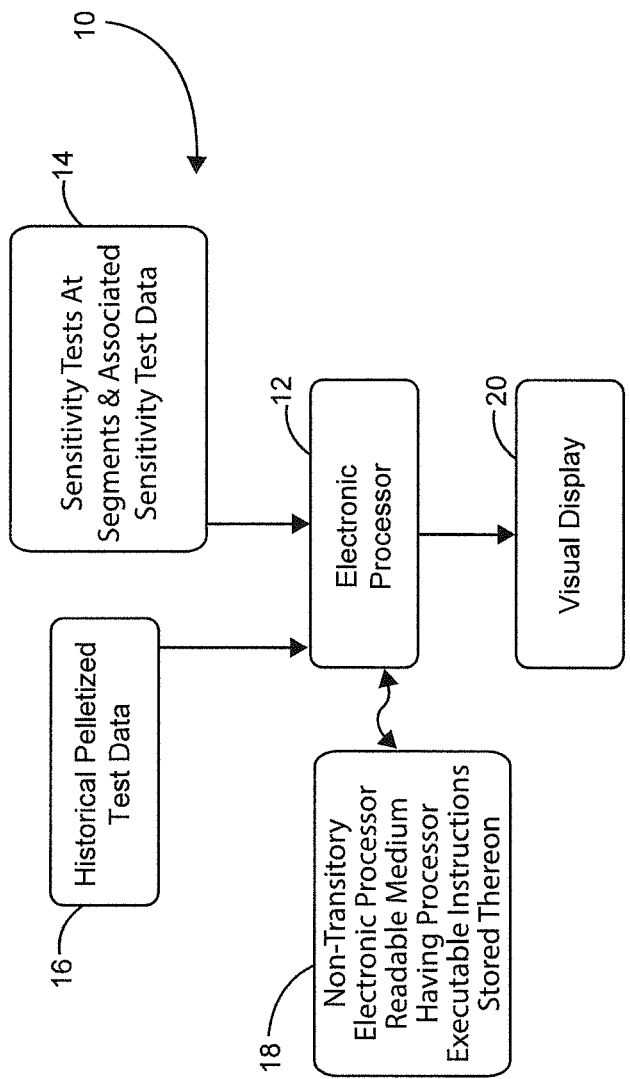
FIG. 1A illustrates a system and its operational components for cumulative distribution function determination, according to some embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention calculate the actual shape of a cumulative distribution function (CDF) by conducting tests at predetermined levels, thereby allowing precise determination of the 50 percent sensitivity level and associated confidence interval.

For background, Bruceton analysis, also known as the "Up and Down Test" or "the staircase method," relies upon two parameters: (1) stimulus and (2) step size. A stimulus, which is some form of energy depending on application-specific conditions, is provided to the sample, and the results noted. When a positive result is noted, then the stimulus is decremented by the step size. When a negative result occurs, the stimulus is increased. The test continues with each sample tested at a stimulus 1 step up or down from the previous stimulus if the previous result was negative or positive. For explosive sensitivity tests, a Gap Test apparatus described in the above-mentioned documents uses attenuator cards with a standard explosive donor charge. Decreasing the number of attenuator cards increases the stimulus to the material under test and likewise, increasing the number of attenuator cards decreases the stimulus to the material under test. The results are then tabulated and analyzed via Bruceton analysis, a simple computation of sums that can be performed by pencil and paper providing estimates of the mean and standard deviation. Confidence estimates are also produced.

The Cumulative Distribution Function (CDF) will in general be a monotonic function but not necessarily symmetric. The drawback with the Bruceton method is that the results will be influenced by the shape of the CDF, the starting point of the test relative to the CDF, and the number of tests performed. Therefore, the Bruceton method would yield the most accurate result with a CDF that approaches a step function, centered about some value. As the shape of the CDF diverges from this ideal, the result will likewise decrease in accuracy.

Although embodiments of the invention are described in considerable detail, including references to certain versions thereof, other versions are possible. Examples of other versions include performing the tasks in an alternate sequence or hosting embodiments on different platforms. Therefore, the spirit and scope of the appended claims should not be limited to the description of versions included herein.

A person having ordinary skill in the art of statistics will recognize that probit modeling is a type of regression where the dependent variable takes one of two values. The model estimates probability that an observation having certain characteristics will fall into one of the categories (one of the two values). When estimated values greater than are treated as an observation into a predicated category, the probit model is a binary classification model.

Embodiments of the invention include calculating the actual shape of the CDF by conducting the tests at predetermined levels, thereby allowing precise determination of the 50% sensitivity level and associated confidence interval. Embodiments of the invention are equally applicable to method and articles of manufacture embodiments. Article of manufacture embodiments are directed to non-transitory processor readable medium(s) having stored thereon processor executable instructions that, when executed by the processor(s), cause the processor to perform the process(es) described herein.

The term non-transitory processor readable medium include one or more non-transitory processor-readable medium (devices or media) having stored thereon a plurality of instructions that, when executed by the electronic processor (typically a central processing unit—an electronic circuit which executes computer programs, containing a processing unit and a control unit), cause the processor to process/manipulate/act on data according to the plurality of instructions (defined herein using the process/function form). The non-transitory medium can be any non-transitory processor readable medium (media), including, for example, a magnetic storage media, "floppy disk," CD-ROM, RAM, a PROM, an EPROM, a FLASH-EPROM, NOVRAM, any other memory chip or cartridge, a file server providing access to the programs via a network transmission line, and a holographic unit. Of course, those skilled in the art will recognize that many modifications may be made to this configuration without departing from the scope.

In some system embodiments, the electronic processor is co-located with the processor readable medium. In other system embodiments, the electronic processor is remotely located from the processor readable medium. It is noted that the steps/acts/processes/tasks described herein including the figures can be interpreted as representing data structures or sets of instructions for causing the computer readable medium to perform the step/act/process.

Certain embodiments of the invention may take the form of non-transitory processor readable mediums having computer-usable/readable program instructions embodied in the medium. Any suitable computer readable medium may be utilized including either computer readable storage media, such as, for example, hard disk drives, CD-ROMs, optical storage devices, or magnetic storage devices, or a transmission media, such as, for example, those supporting the internet or intranet.

Computer-usable/readable program instructions for carrying out operations of embodiments of the invention may be written in an object oriented programming language such as, for example, Python, Visual Basic, or C++. However, computer-usable/readable program instructions for carrying out operations of embodiments of the invention may also be written in conventional procedural programming languages, such as, for example, the C or C# programming languages or an engineering prototyping language such as, for example, MATLAB®. However, the concepts may be replicated for many platforms provided that an appropriate compiler is used.

The computer-usable/readable program instructions may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider or any other method known in the art).

Embodiments of the invention are described in part below with reference to flow chart illustrations and/or block diagrams of methods and computer program products according to embodiments of the invention. It will be understood that each block of the flow chart illustrations and/or block diagrams, and combinations of blocks in the flow chart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks.

These computer program instructions may also be stored in a computer-readable memory, including RAM, that can direct a computer or other programmable data processing apparatus to function in a particular manner, such that the instructions stored in the computer-readable memory produce an article of manufacture including instructions that implement the function/act specified in the flow chart and/or block diagram block or blocks.

These computer program instructions may also be loaded onto a computer or other programmable data processing apparatus to cause a series of operational tasks to be performed on the computer or other programmable apparatus to produce a computer implemented process such that the instructions that execute on the computer or other programmable apparatus provide tasks for implementing the functions/acts specified in the flow chart and/or block diagram block or blocks.

In the accompanying drawings, like reference numbers indicate like elements. FIG. 1A illustrates a system and its operational components for cumulative distribution function determination of energetic sensitivity. Reference character 10 depicts a system of embodiments of the invention. The system 10, may also be referred to as an apparatus, method, or a combination of both apparatus and method for shorthand purposes, without detracting from the merits or generality of embodiments of the invention.

Embodiments of the invention generally relate to a system for determining the actual shape of a cumulative distribution function (CDF) for an energetic composition. The system 10 includes at least one electronic processor having a central processing unit 12. The central processing unit (CPU), and computer memory are electrically connected to the computer's motherboard. A graphics processing unit (GPU) may also be employed in some embodiments of the invention are in those embodiments, the GPU is also electrically connected with the motherboard. In some applications, depending on the verification requirements, a visual verification by a user may be important to provide an additional layer of validation before acting on the processing result.

A grouping of sensitivity tests at particularized segments and sensitivity test data 14 associated with said grouping of sensitivity tests data is configured for input into the electronic processor 12. Historical pelletized explosive test data 16 corresponding to previous test data performed on the energetic composition is configured for input to the electronic processor 12.

An energetic determination tool 18 is associated with the electronic processor 12. The energetic determination tool 18 is configured to determine the actual shape of a cumulative distribution function (CDF) associated with the energetic composition. The determination of the actual shape of the CDF allows for more accurate determination of the 50 percent energetic sensitivity level of the energetic composition. At least one device 20 is associated with the electronic processor 12 and is configured to output the actual shape of the CDF in a tangible medium such as a visual display screen. The actual shape of the CDF would be displayed, for example, on an x-y axis plot with the x-axis depicting a range of the particularized segments, which are the number of attenuator cards from zero to about 300 cards. The y-axis depicts sensitivity probabilities of the energetic composition. Although numerous other tangible mediums for output include hard copy prints as well as other media configured to use output from embodiments of the invention.

Figure 1B:
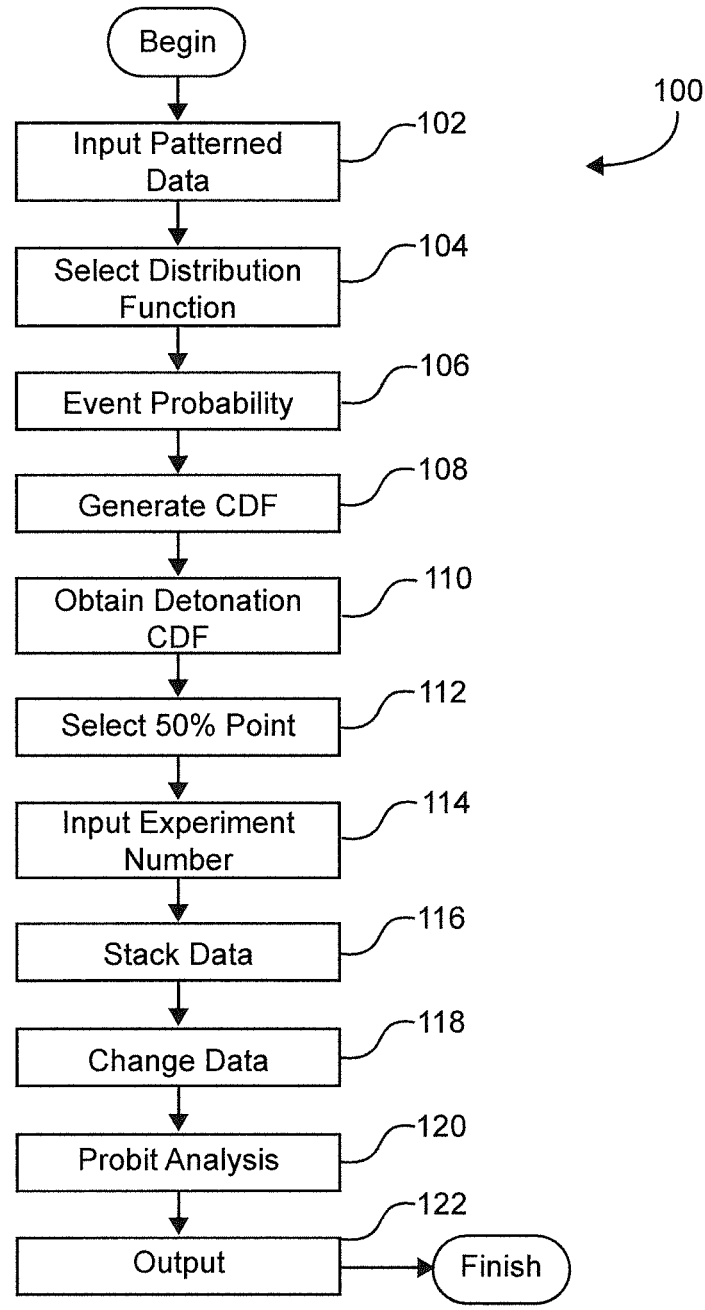
FIG. 1B is an exemplary flowchart illustrating tasks for simulating the actual shape of a cumulative distribution function, according to some embodiments of the invention.
Figure 1C:
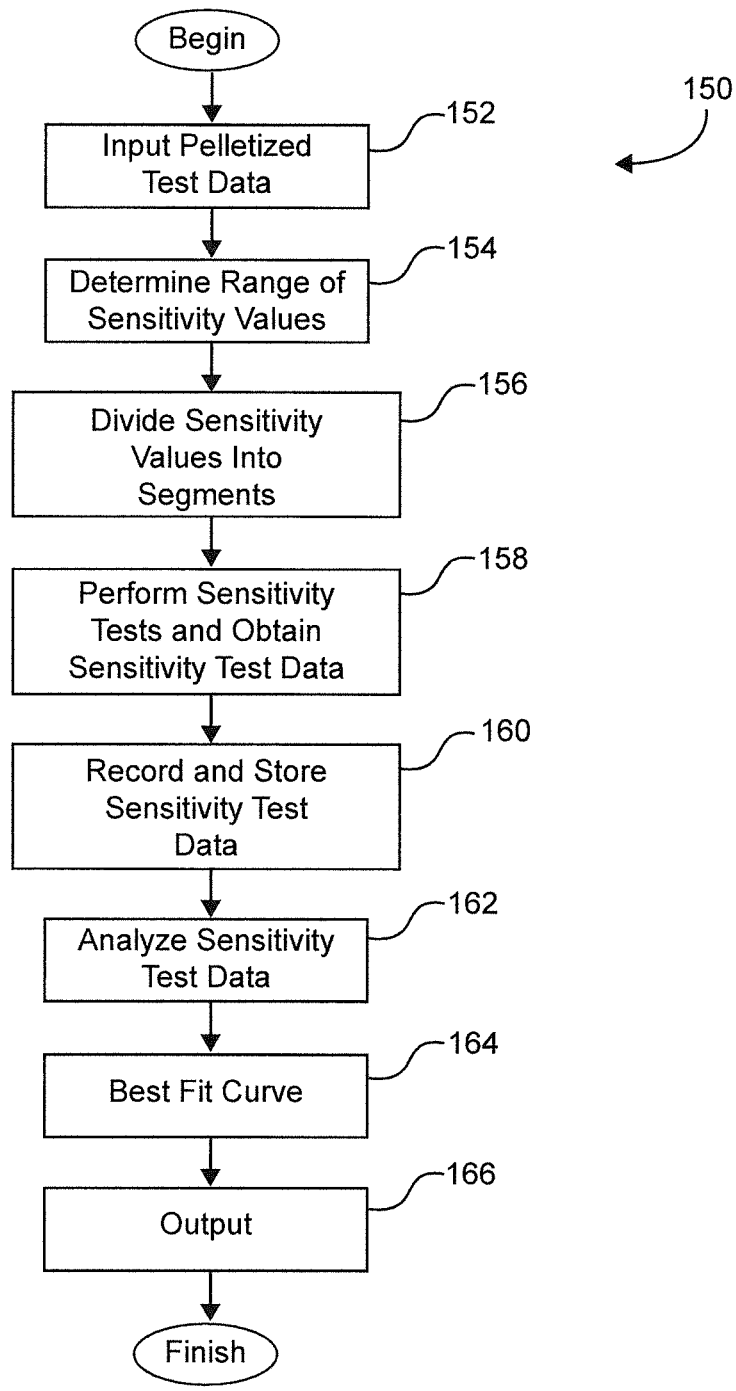
FIG. 1C is an exemplary flowchart illustrating the tasks for cumulative distribution function determination, according to some embodiments of the invention.

FIGS. 1B & 1C are equally applicable to methods and articles of manufacture associated with embodiments of the invention. Reference characters 100 and 150 are used to refer to both methods and articles of manufacture in FIGS. 1B & 1C, respectively.

Referring to both FIGS. 1A & 1C, the energetic determination tool is a non-transitory electronic-processor-readable medium having a plurality of electronic processor executable instructions stored thereon. The executable instructions when executed by the electronic processor 12, causes the processor to perform several tasks to obtain the actual shape of the cumulative distribution function (CDF) for the energetic composition. The electronic processor 12 includes a data storage device.

As shown in FIG. 1C, as depicted in task 152, historical pelletized explosive test data is input into an electronic processor. In task 154, a range of sensitivity values is determined for the energetic composition. The range is selected based on the historical pelletized explosive test data for similar energetic composition formulations. The range is selected by the user or in some embodiments, the electronic processor executable instructions select the range based on the historical pelletized explosive test data. The range is bounded by sensitivity endpoints.

In task 156, the sensitivity values are divided into at least three segments between the sensitivity endpoints. The segments may be equally spaced or not equally spaced. The segments correspond to predetermined sensitivity levels based on the historical pelletized explosive data. In some embodiments, the selected number of segments is three. In other embodiments, the selected number of segments is four.

In task 158, sensitivity tests are electronically performed simulations at each of the segments (at least three segments). The target number of tests at each of the segments is about ten tests per segment. Of course, it is understood that more than or less than ten tests per segment may be performed based on historical data. The sensitivity tests yield sensitivity test data. The sensitivity test data is electronically-recorded and stored in memory associated with the electronic processor 12 (task 160).

In task 162, the sensitivity test data is electronically analyzed by the electronic processor 12. The analysis in task 162 is a probit analysis that stacks response data with a corresponding stimulus level for each response entry. The probit analysis is performed by stacking all response data in one column with corresponding stimulus level for each response entry in an adjacent column. The number of events is then converted to a percentage. An example of converting the stimulus to a percent would be performing statistical analysis by entering the column with the particular data into a variables box, such as a first windows box and the column with the stimulus levels into a second windows box. Statistical variance and mean can be calculated.

The response data occurs where detonation is exhibited in the energetic composition. Probability distributions can be examined including smallest extreme value, Weibull, Normal, Lognormal, logistic, or loglogistic, that possess a correlation coefficient closest to one (1). The probit analysis is performed with the selected distribution. Response and stimulus levels are processed. This results in a probability plot showing the fitted percent probability versus stimulus level, the stimulus levels relative to the fitted probability, and the confidence intervals associated with the fitted probability.

Task 164 electronically fits a best fit curve through data points corresponding to the proportion of detonation events of the energetic composition. The best fit curve is output in task 166 in the tangible medium described earlier, such as on the visual display screen 20. Outputting of the best fit curve includes visually displaying the fitted percent probability versus stimulus level, stimulus levels relative to the fitted probability, and the confidence intervals associated with the fitted probability.

In yet another embodiment, as depicted in FIG. 1B, depicted as reference character 100, a method for simulating the actual shape of a cumulative distribution function (CDF) that describes the energetic sensitivity of an energetic composition is shown. The method lends itself to validating test methods and previously performed analysis of the energetic composition. The output produced by the method determines the 50 percent energetic sensitivity level of the energetic composition.

Historical pelletized explosive test data is input into the electronic processor. The grouping of sensitivity tests at particularized segments and the patterned sensitivity test data is input into the electronic processor (task 102). The patterned sensitivity test data has the parameters of a plurality of attenuator cards ranging from zero to 300 attenuator cards and an event probability value corresponding to each attenuator card in the plurality of attenuator cards. The range of sensitivity values is defined from zero to 300 attenuator cards. Sensitivity endpoints occur at both zero and 300 attenuator cards. The range of sensitivity values is divided into at least three segments between the sensitivity endpoints. The three segments correspond to the predetermined sensitivity levels based on the historical pelletized explosive data.

In task 104, a distribution function is selected for the patterned sensitivity test data. Some distribution functions that can be selected are discussed and illustrated in detail in FIGS. 2 through 12. An event probability is determined for the distribution function (task 106). In task 108, cumulative distribution function (CDF) data is generated that corresponds to the event probability. Task 110 determines a detonation CDF of the generated CDF data. A desired 50 percent energetic sensitivity level of the detonation CDF is selected in task 112. The desired 50 percent energetic sensitivity level corresponds to at least three segments for random data creation. The random data creation is useful for simulating processes.

In task 114, a number of simulated sensitivity test experiments are determined. The simulated sensitivity test experiments correspond to each of the at least three segments. The number of simulated sensitivity test experiments are input into the electronic processor. The electronic processor is instructed to electronically simulate the sensitivity tests the determined number of times at each of the at least three segments. The simulated sensitivity test experiments produce simulated sensitivity test data that is electronically recorded and stored in the electronic memory associated with the electronic processor.

The simulated test data is converted (changed), if necessary, from a text to a numeric data format. The simulated sensitivity test data is electronically analyzed. The analysis provides response data points. The data response data points correspond to a proportion of detonation events at the simulated sensitivity tests at each of the at least three segments. Response data is stacked with a corresponding stimulus level for each response entry. The response data is the response data points corresponding to the proportion of detonation events. The stimulus level is energy applied to the energetic composition. A best fit curve is electronically fit through the response data points. The best fit curve is defined as the actual shape of the CDF.

The best fit curve is output in the tangible medium. Included in the analysis is the automated of corresponding attenuator card values corresponding to the 50 percent energetic sensitivity value from the best fit curve. The card value (the number of cards at which the 50 percent point is located) is also produced as output (tasks 116 through 122).

Scenarios can, of course, occur when historical pelletized explosive test data is not available for a particular energetic composition. In scenarios such as those, physical testing is performed on the energetic composition. The physical testing produces pelletized test results for the energetic composition. The pelletized test results are then labeled and stored as historical pelletized test data and configured for input into the electronic processor 12.

The physical testing performed on the energetic composition when historical pelletized explosive test data does not exist is a gap test. A gap test is conducted with a first endpoint of zero attenuator cards and a second endpoint of three inches of cards. The first and second endpoints are defined as extremes. The attenuator cards are about 0.01 inches thick and are constructed of Plexiglass® or similar material. One having ordinary skill in the art will recognize that Plexiglass® is a poly methyl methacrylate (PMMA) and is a transparent thermoplastic, sometimes called acrylic glass, that is a lightweight or shatter-resistant alternative to glass.

The concept is to fill up space with the cards until detonation of the energetic composition occurs. All the predetermined levels of testing are then conducted using the gap test. The data is obtained and then the best fit curve procedure (the output), as described above is performed. When an event (detonation of the energetic composition) is not recorded at zero gap (zero attenuator cards) or an event is recorded at three inches of gap (300 attenuator cards), the test is defined as inappropriate because the data is not actionable because it is located at the extremes.

For the physical testing, the samples are prepared by being pressed into pellets to test at regions between the extremes. A target number of tests is one test at about every 0.3 inches of gap between the first and second endpoint (between zero and three inches of attenuator cards). When an event is not recorded at zero gap or an event is recorded at three inches of gap, the test is defined as inappropriate. A range is selected between gap values where an event is first noted and where events occur repeatedly.

FIGS. 2 Through 12

Significant modeling was performed on embodiments of the invention. FIGS. 2 through 12 illustrate some of the modeling, as illustrated on the visual display screen or hardcopy printouts. The curves shown in FIGS. 2 through 12 have different underlying probability distributions. Different energetic composition materials behave differently. The CDF is chosen that most closely mimics the energetic material of interest. The modeling includes substantial statistical analysis to determine event probabilities for increasing attenuator card values according to the relationship of: event probability=1−CDF. The particular CDF values are obtained according to individualized statistical analysis based historical data and the number of parameters.

The embodiments of the invention fit a curve to data points and can then read an exact 50 percent sensitivity level (the number of attenuator cards at a 50 percent probability). For FIGS. 2 through 12, the x-axis represents the attenuator cards and the y-axis represents the probability values from 0 to 1.0 (0 percent to 100 percent). Each time a simulation is performed, a curve is fit to the respective data points which allows the determination of the 50 percent sensitivity level (the 50 percent probability) at that simulation. This allows for multiple simulations to be performed.

The modeling employs unitless parameter numbers for shape, threshold, and scale, according to which distribution is being modeled. A scale example includes standard deviation. A threshold example includes mean. Parametric probability distributions have the properties of shape, scale, and location. Shape, as the name implies, will fundamentally change the shape of the distribution. The modeled distributions are as shown in FIGS. 2 through 12.

For some corresponding event probabilities of increasing card values (task 106), the CDF is determined by $$CDF = e^{-\left(\frac{x-location}{scale}\right)}.$$

The larger the scale, the more gradual the CDF appears between probabilities of one and zero. As an example, trying a scale of 10 to start, the location is calculated by location=scale(−ln(−ln(0.5))+desired 50% point).

Figure 2:
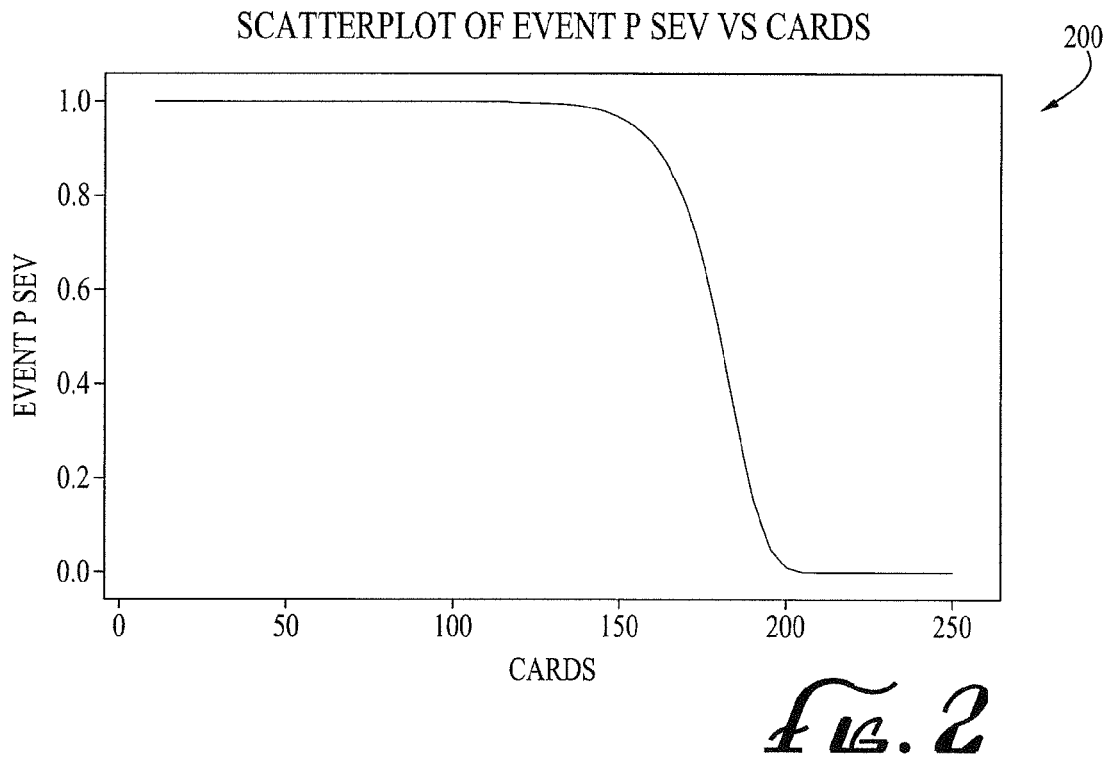
FIG. 2 illustrates a scatter plot of probability events (smallest extreme value) at a corresponding number of attenuator cards, a smallest extreme value CDF, according to some embodiments of the invention.

FIG. 2 illustrates a smallest extreme value CDF, as depicted by reference character 200. The smallest extreme value CDF is determined by $$CDF = e^{-\left(\frac{x}{scale}\right)^{shape}}.$$

The larger the shape, the less gradual the CDF appears between the probabilities of one and zero. Trying a shape of 10 to start, the scale is calculated by scale=$e^{ln(ln(desired\ 50\%\ point)-ln(-ln(0.5))/shape)}$.

Figure 3:
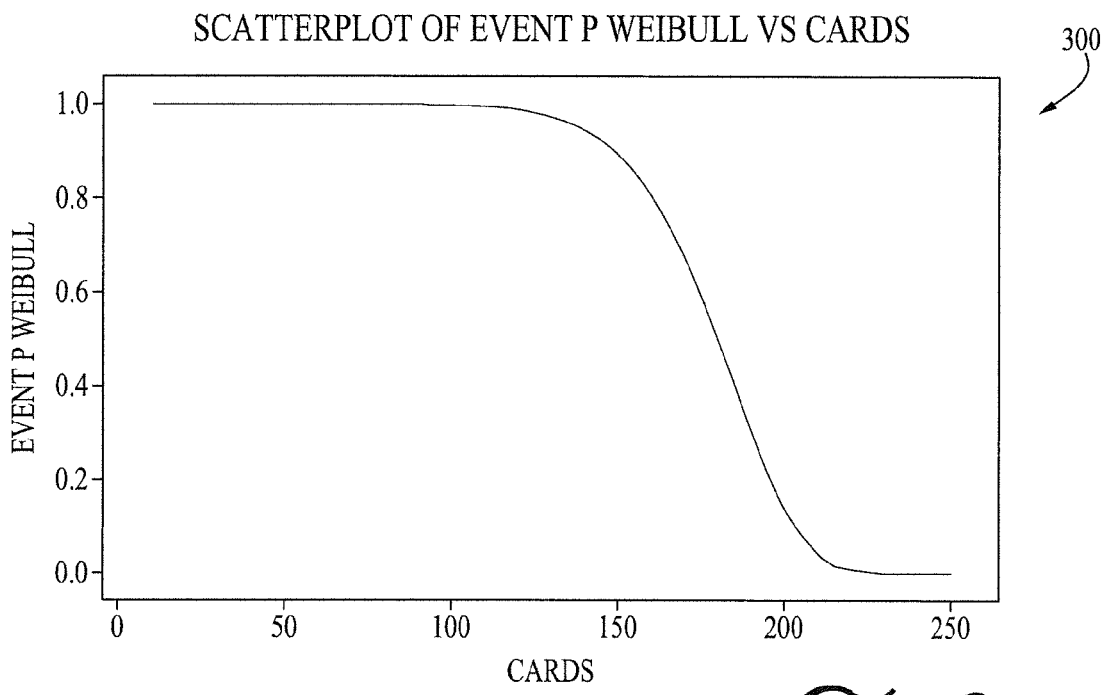
FIG. 3 illustrates a scatter plot of probability events P at a corresponding number of attenuator cards, a Weibull CDF, according to some embodiments of the invention.

FIG. 3 illustrates a Weibull CDF, as depicted by reference character 300. The Weibull CDF is determined by $$CDF = e^{-\left(\frac{x-threshold}{scale}\right)^{shape}}.$$

The larger the shape, the less gradual the CDF appears between the probabilities of one and zero. Trying a shape of 10 to start, the scale is calculated by scale=$e^{ln(ln(desired\ 50\%\ point-threshold)-ln(-ln(0.5))/shape)}$.

Figure 4:
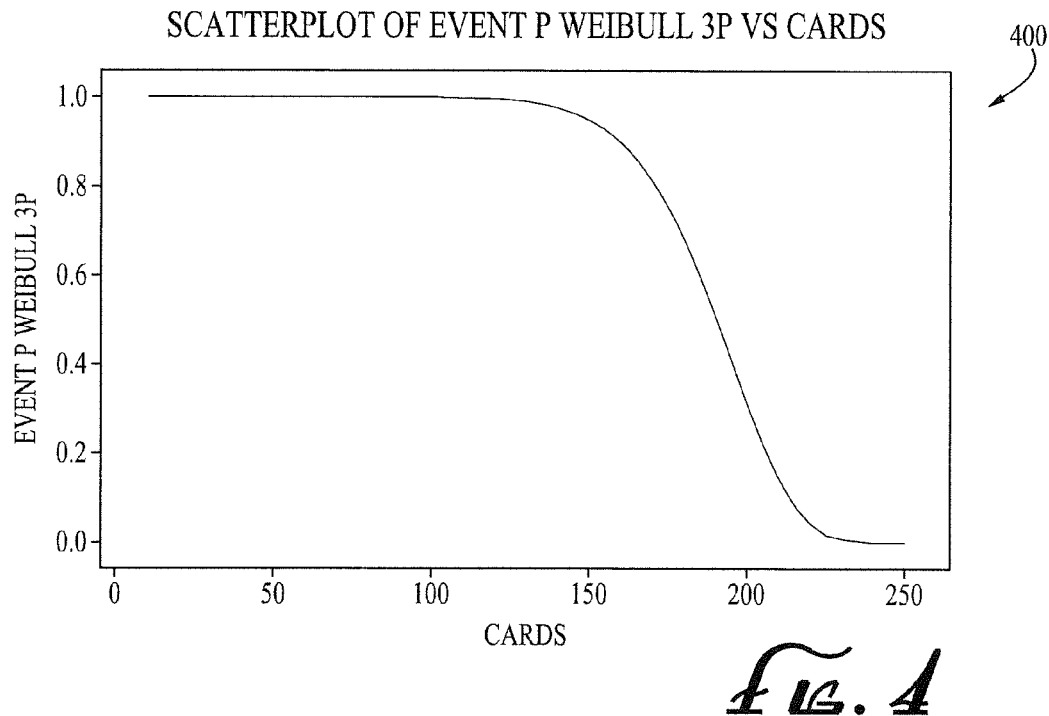
FIG. 4 illustrates a scatter plot of probability events P at a corresponding number of attenuator cards, a 3 parameter Weibull CDF, according to some embodiments of the invention.

FIG. 4 illustrates a 3 parameter Weibull CDF, as depicted by reference character 400. The 3 parameter Weibull CDF is determined by $$CDF = e^{-\left(\frac{x}{scale}\right)}.$$

The larger the scale, the more gradual the slope of the function as it approaches 0. The scale is calculated by $$scale = -\frac{(\text{desired 50\% point})}{\ln(.5)}.$$

Figure 5:
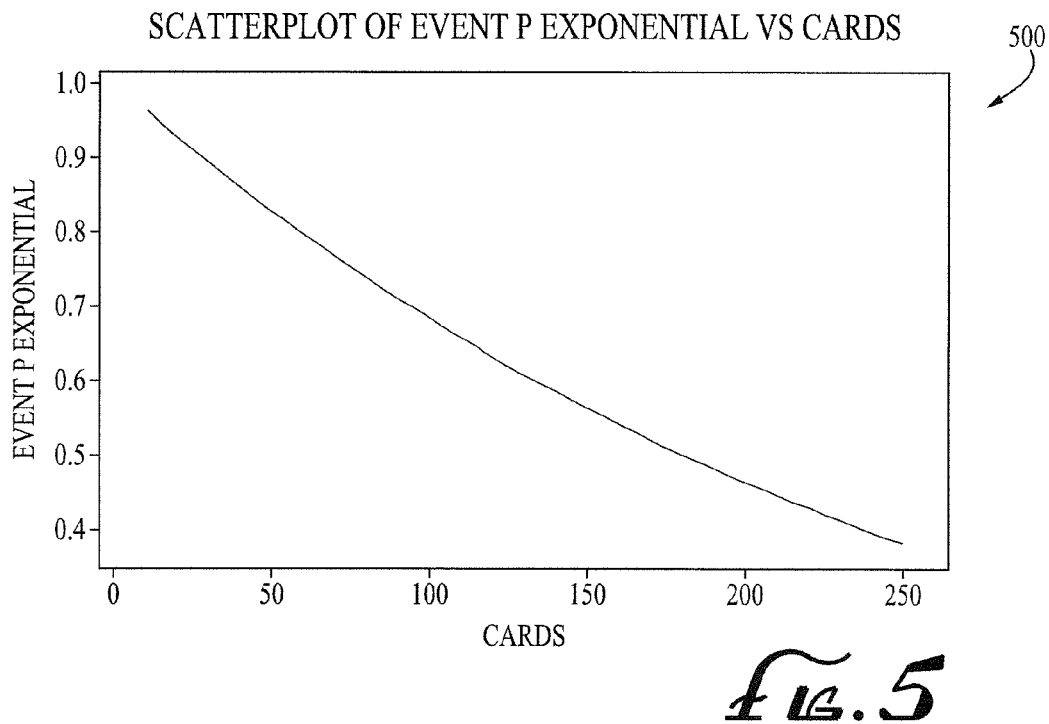
FIG. 5 illustrates a scatter plot of probability events P at a corresponding number of attenuator cards, an exponential CDF, according to some embodiments of the invention.

FIG. 5 illustrates an exponential CDF, as depicted by reference character 500. The exponential CDF is determined by $$CDF = e^{-\left(\frac{x-threshold}{scale}\right)}.$$

The larger the scale, the more gradual the slope of the function as it approaches 0. The scale is calculated by $$scale = -\frac{(\text{desired 50\% point} - \text{threshold})}{\ln(.5)}.$$

Figure 6:
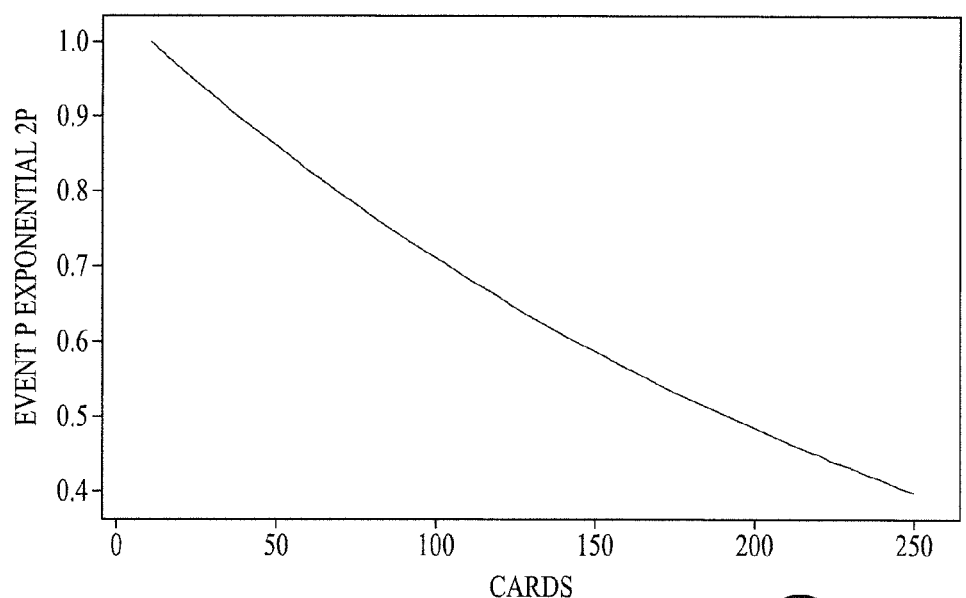
FIG. 6 illustrates a scatter plot of probability events P at a corresponding number of attenuator cards, a 2 parameter exponential CDF, according to some embodiments of the invention.

FIG. 6 illustrates a 2 parameter exponential CDF, as depicted by reference character 600. The 2 parameter exponential CDF is determined using the complementary error function by $$CDF = 1 - (0.5)\text{erfc}\left(-\left(\frac{x - \text{location}}{\sqrt{2}\ scale}\right)\right).$$

The larger the scale, the more gradual the CDF appears between the probabilities of one and zero. Trying a scale of location/10 to start, the desired 50% point is the location value.

Figure 7:
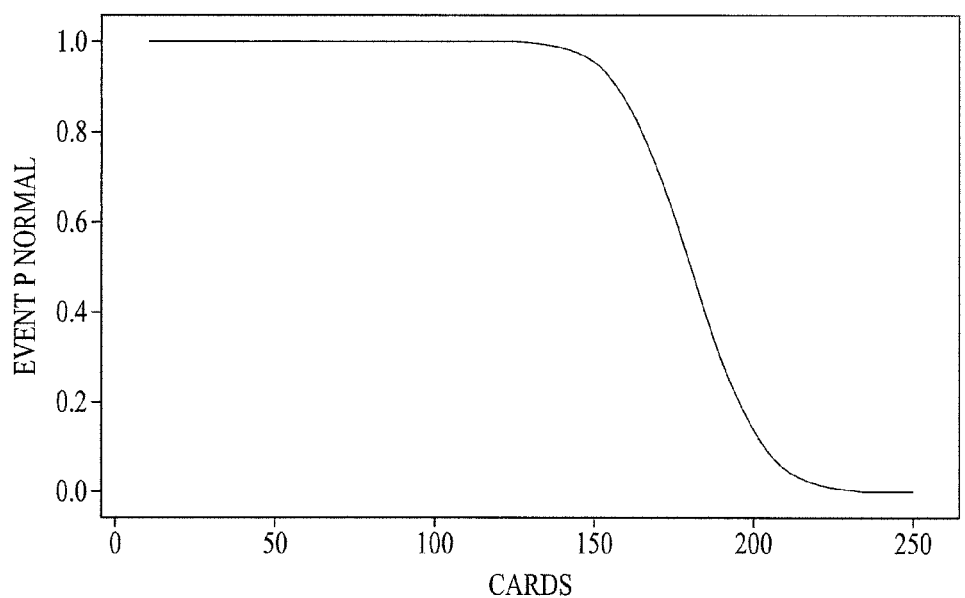
FIG. 7 illustrates a scatter plot of probability events P at a corresponding number of attenuator cards, a normal CDF, according to some embodiments of the invention.

FIG. 7 illustrates a normal CDF, as depicted by reference character 700. The normal CDF is also determined using the complementary error function by $$CDF = 1 - (0.5)\text{erfc}\left(-\left(\frac{\ln(x) - \text{location}}{\sqrt{2}\ scale}\right)\right).$$

The larger the scale, the more gradual the CDF appears between the probabilities of one and zero. Trying a scale of location/10 to start, the location is calculated to be ln(desired 50% point). The argument of the natural logarithm must be greater than zero. Therefore, attenuator card values are greater than zero.

Figure 8:
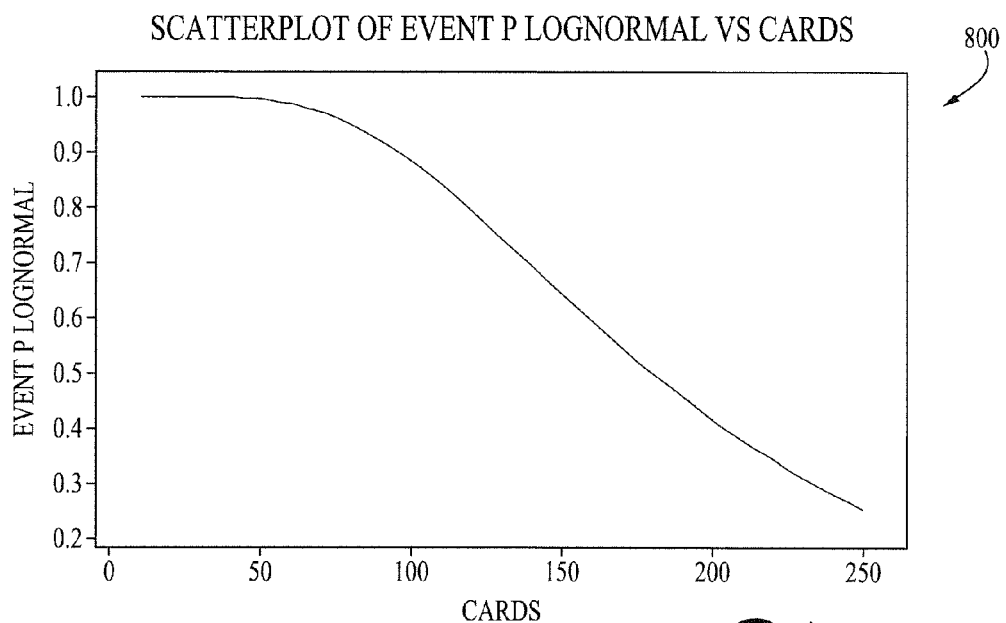
FIG. 8 illustrates a scatter plot of probability events P at a corresponding number of attenuator cards, a lognormal CDF, according to some embodiments of the invention.

FIG. 8 illustrates a lognormal CDF, as depicted by reference character 800. The lognormal CDF is also determined using the complementary error function by $$CDF = 1 - (0.5)\text{erfc}\left(-\left(\frac{\ln(x - \text{threshold}) - \text{location}}{\sqrt{2}\ scale}\right)\right).$$

The larger the scale, the more gradual the CDF appears between the probabilities of one and zero. Trying a scale of location/10 to start, the location is calculated to be ln(desired 50% point−threshold). The argument of the natural logarithm must be greater than zero. Therefore, attenuator card values are greater than zero.

Figure 9:
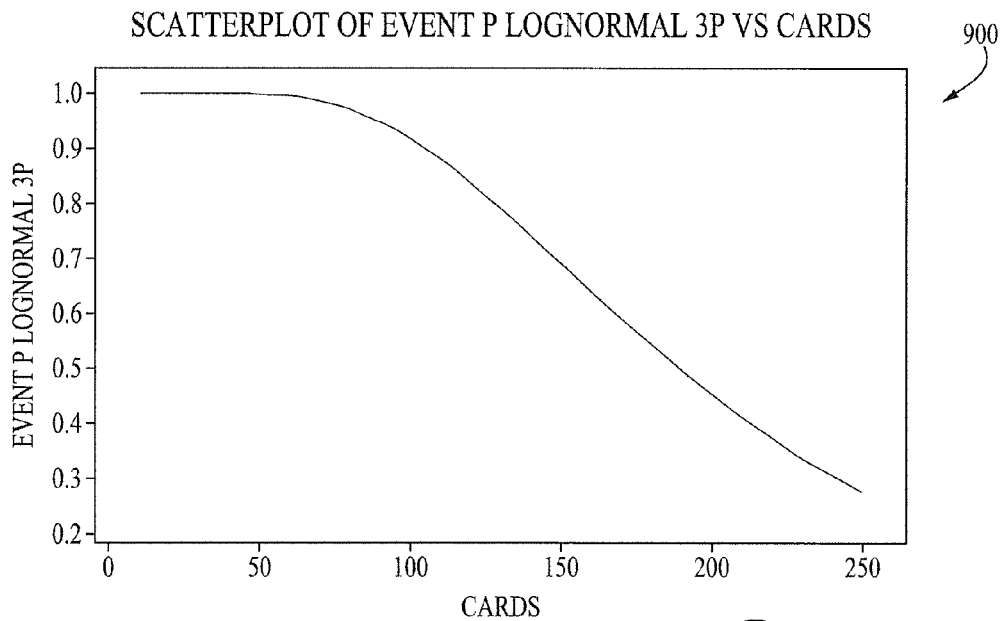
FIG. 9 illustrates a scatter plot of probability events P at a corresponding number of attenuator cards, a 3 parameter lognormal CDF, according to some embodiments of the invention.

FIG. 9 illustrates a 3 parameter lognormal CDF, as depicted by reference character 900. The 3 parameter lognormal CDF is determined by $$CDF = 1 - \left(\frac{1}{1 + e^{-(x - \text{location})/scale}}\right).$$

The larger the scale, the more gradual the CDF appears between the probabilities of one and zero. Trying a scale of location/10 to start, the desired 50 percent point is the location value.

Figure 10:
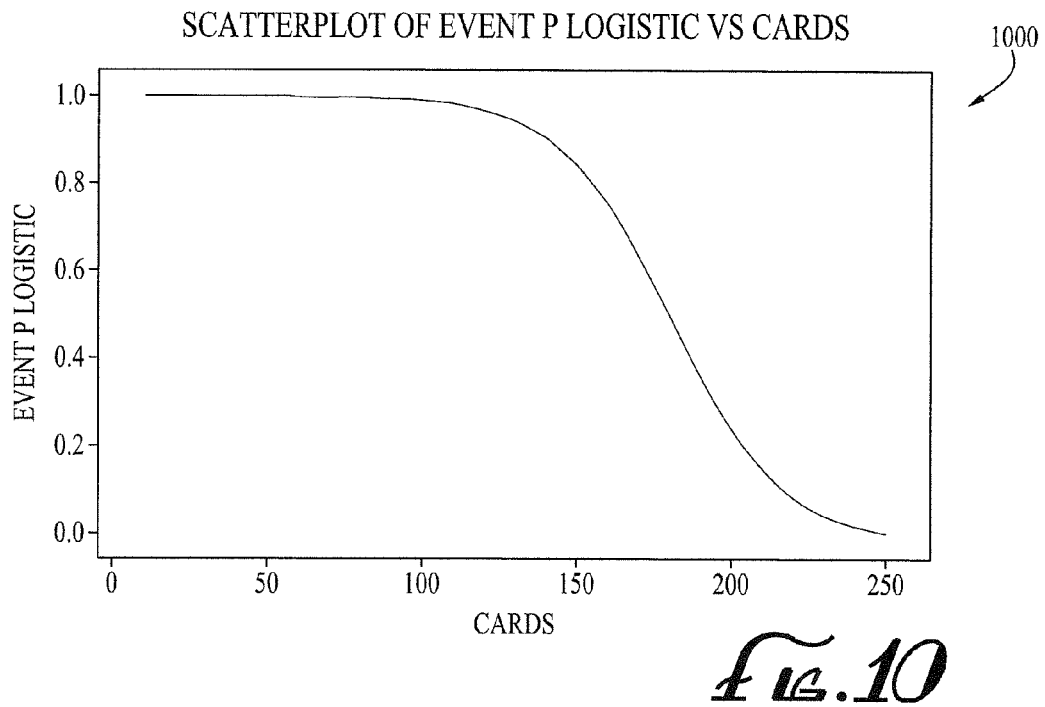
FIG. 10 illustrates a scatter plot of probability events P at a corresponding number of attenuator cards, a logistic CDF, according to some embodiments of the invention.

FIG. 10 illustrates a logistic CDF, as depicted by reference character 1000. The logistic CDF is determined by $$CDF = 1 - \left(\frac{1}{1 + e^{-\left(\frac{\ln(x) - \text{location}}{scale}\right)}}\right).$$

The larger the scale, the more gradual the CDF appears between the probabilities of one and zero. Trying a scale of location/10 to start, the location is calculated to be ln(desired 50% point). The argument of the natural logarithm must be greater than zero. Therefore, attenuator card values are greater than zero.

Figure 11:
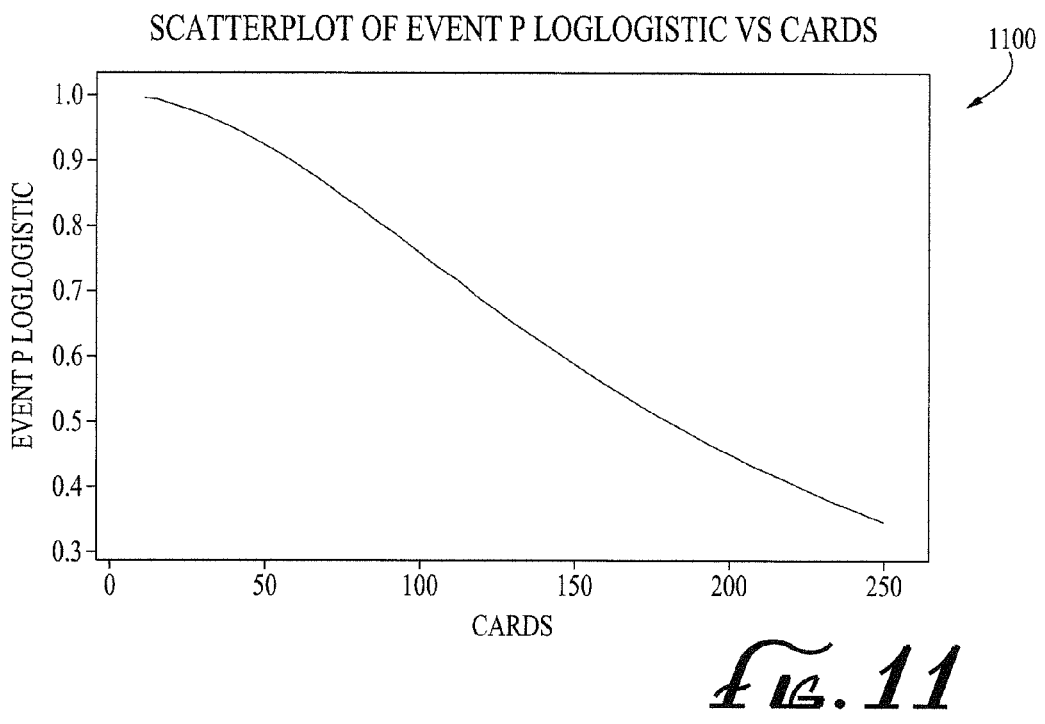
FIG. 11 illustrates a scatter plot of probability events P at a corresponding number of attenuator cards, a loglogistic CDF, according to some embodiments of the invention.

FIG. 11 illustrates a loglogistic CDF, as depicted by reference character 1100. The loglogistic CDF is determined by $$CDF = 1 - \left(\frac{1}{1 + e^{-\left(\frac{\ln(x - threshold) - \text{location}}{scale}\right)}}\right).$$

The larger the scale, the more gradual the CDF appears between the probabilities of one and zero. Trying a scale of location/10 to start, the location is calculated to be ln(desired 50% point−threshold). The argument of the natural logarithm must be greater than zero. Therefore, attenuator card values are greater than zero.

Figure 12:
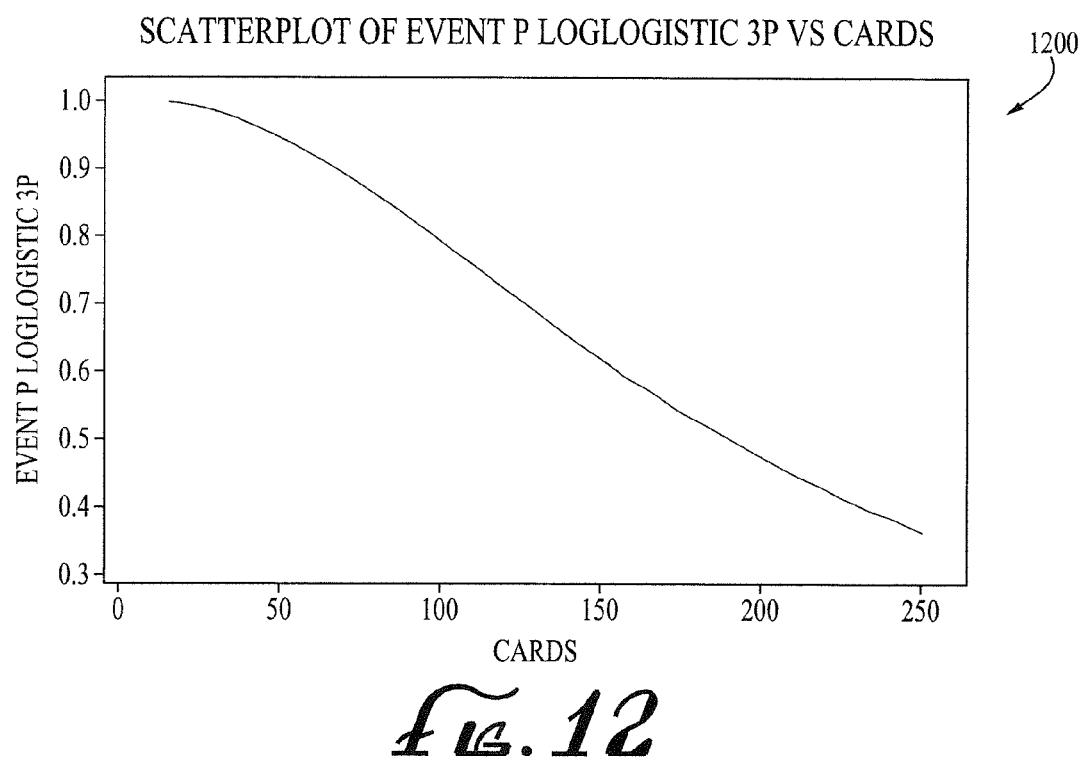
FIG. 12 illustrates a scatter plot of probability events P at a corresponding number of attenuator cards, a 3 parameter loglogistic CDF, according to some embodiments of the invention.

FIG. 12 illustrates a 3 parameter loglogistic CDF, as depicted by reference character 1200. The 3 parameter loglogistic CED is determined by $$CDF = 1 - \left(\frac{1}{1 + e^{-\left(\frac{\ln(x - threshold) - \text{location}}{scale}\right)}}\right).$$

The larger the scale, the more gradual the CDF appears between the probabilities of one and zero. Trying a scale of location/10 to start, the location is calculated to be ln(desired 50% point−threshold).

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A system for determining sensitivity of at least one energetic composition material to explosive shock using an energetic determination tool to simulate an actual shape of a cumulative distribution function (CDF) for said at least one energetic composition material, said system comprising:
- at least one electronic processor having a central processing unit (CPU) and associated electronic memory;
- a graphics processing unit (GPU) associated with said CPU;
- a grouping of sensitivity tests at particularized segments and patterned sensitivity test data associated with said grouping of sensitivity tests, said grouping of sensitivity tests at particularized segments and said patterned sensitivity test data associated with said at least one energetic composition material, said grouping of sensitivity tests at particularized segments and said patterned sensitivity tests data configured for input to said at least one electronic processor;
- historical pelletized explosive test data corresponding to previous test data performed on said at least one energetic composition material, said historical pelletized explosive test data configured for input to said at least one electronic processor;
- an energetic determination tool associated with said at least one electronic processor, wherein said energetic determination tool is configured to simulate an actual shape of a cumulative distribution function (CDF) associated with said at least one energetic composition material; and
- at least one device associated with said at least one electronic processor configured to output in a tangible medium the actual shape of said CDF;
- wherein said energetic determination tool is a non-transitory electronic-processor-readable medium having a plurality of electronic processor executable instructions stored thereon, that when executed by said at least one electronic processor, causes said at least one electronic processor to:
  - input said historical pelletized explosive test data into said at least one electronic processor;
  - input said grouping of sensitivity tests at particularized segments and said patterned sensitivity test data into said at least one electronic processor, said patterned sensitivity test data having parameters of a plurality of attenuator cards ranging from zero to 300 attenuator cards and an event probability value corresponding to each of said attenuator card in said plurality of attenuator cards, wherein plurality of attenuator cards ranging from zero to 300 attenuator cards are defined as a range of sensitivity values, said range of sensitivity values bounded by sensitivity endpoints, wherein said range is divided into at least three segments between said sensitivity endpoints, said at least three segments corresponding to predetermined sensitivity levels based on said historical pelletized explosive data;
  - select a distribution function for simulating said patterned sensitivity test data;
  - determine an event probability for said distribution function;
  - generate cumulative distribution function (CDF) data corresponding to said event probability;
  - determine a detonation CDF of said generated CDF data;
  - select a desired 50 percent energetic sensitivity level of said detonation CDF, said desired 50 percent energetic sensitivity level corresponding to said at least three segments for random data creation;
  - determine a number of simulated sensitivity test experiments corresponding to each of said at least three segments and input said number of simulated sensitivity test experiments into said at least one electronic processor, and electronically simulate sensitivity tests said number of times at each of said at least three segments, said simulated sensitivity test experiments producing simulated sensitivity test data, wherein said simulated sensitivity test data is electronically recorded and stored in said electronic memory;
  - electronically determine a CDF by analyzing said simulated sensitivity test data, wherein said analysis provides response data points, said response data points corresponding to a proportion of detonation events at said simulated sensitivity tests at each of said at least three segments;
  - stack said response data with a corresponding stimulus level for each response entry, wherein said response data are said response data points corresponding to said proportion of detonation events, wherein said stimulus level is energy applied to said at least one energetic composition material;
  - electronically fit a best fit curve through said response data points, wherein said best fit curve is defined as the actual shape of said CDF;
  - output said best fit curve in said tangible medium; and
  - obtain said at least one energetic composition material corresponding to the actual shape of said CDF.

2. The system according to claim 1, wherein said output of said best fit curve further comprising visually displaying a fitted percent probability versus stimulus level, stimulus levels relative to the fitted probability, and the confidence intervals associated with the fitted probability.

3. The system according to claim 1, wherein said at least three segments is three segments.

4. The system according to claim 1, wherein said at least three segments is four segments.

5. The system according to claim 1, wherein said analyzing said simulated test data is a probit analysis.

6. The system according to claim 1, wherein said tangible medium is a visual display screen.

7. A method for determining sensitivity of at least one energetic composition material to explosive shock using an energetic determination tool to simulate an actual shape of a cumulative distribution function (CDF) for said at least one energetic composition material using an electronic processor having a central processing unit (CPU) and electronic memory and a graphics processing unit (GPU) associated with said CPU, said method comprising:
- providing a grouping of sensitivity tests at particularized segments and patterned sensitivity test data associated with said grouping of sensitivity tests, said grouping of sensitivity tests at particularized segments and said patterned sensitivity test data associated with said at least one energetic composition material, said grouping of sensitivity tests at particularized segments and said patterned sensitivity tests data configured for input to said at least one electronic processor;
- providing historical pelletized explosive test data corresponding to previous test data performed on said at least one energetic composition material, said historical pelletized explosive test data configured for input to said at least one electronic processor;

providing an energetic determination tool associated with said at least one electronic processor, wherein said energetic determination tool is configured to simulate the actual shape of a cumulative distribution function (CDF) associated with said at least one energetic composition material;

providing at least one device associated with said at least one electronic processor configured to output in a tangible medium the actual shape of said CDF;

inputting said historical pelletized explosive test data into said at least one electronic processor;

inputting said grouping of sensitivity tests at particularized segments and said patterned sensitivity test data into said at least one electronic processor, said patterned sensitivity test data having parameters of a plurality of attenuator cards ranging from zero to 300 attenuator cards and an event probability value corresponding to each of said attenuator card in said plurality of attenuator cards, wherein plurality of attenuator cards ranging from zero to 300 attenuator cards are defined as a range of sensitivity values, said range of sensitivity values bounded by sensitivity endpoints, wherein said range is divided into at least three segments between said sensitivity endpoints, said at least three segments corresponding to predetermined sensitivity levels based on said historical pelletized explosive data;

selecting a distribution function for simulating said patterned sensitivity test data;

determining an event probability for said distribution function;

generating cumulative distribution function (CDF) data corresponding to said event probability;

determining a detonation CDF of said generated CDF data;

selecting a desired 50 percent energetic sensitivity level of said detonation CDF, said desired 50 percent energetic sensitivity level corresponding to said at least three segments for random data creation;

determining a number of simulated sensitivity test experiments corresponding to each of said at least three segments and inputting said number of simulated sensitivity test experiments into said at least one electronic processor, and electronically simulating sensitivity tests said number of times at each of said at least three segments, said simulated sensitivity test experiments producing simulated sensitivity test data, wherein said simulated sensitivity test data is electronically recorded and stored in said electronic memory;

electronically determining a CDF by analyzing said simulated sensitivity test data, wherein said analysis provides response data points, said response data points corresponding to a proportion of detonation events at said simulated sensitivity tests at each of said at least three segments;

stacking said response data with a corresponding stimulus level for each response entry, wherein said response data are said response data points corresponding to said proportion of detonation events, wherein said stimulus level is energy applied to said at least one energetic composition material;

electronically fitting a best fit curve through said response data points, wherein said best fit curve is defined as the actual shape of said CDF;

outputting said best fit curve in said tangible medium; and obtaining said at least one energetic composition material corresponding to the actual shape of said CDF.

8. The method according to claim 7, wherein said outputting of said best fit curve further comprising visually displaying a fitted percent probability versus stimulus level, stimulus levels relative to the fitted probability, and the confidence intervals associated with the fitted probability.

9. The method according to claim 7, wherein said at least three segments is three segments.

10. The method according to claim 7, wherein said at least three segments is four segments.

11. The method according to claim 7, wherein said analyzing said simulated test data is a probit analysis.

12. The method according to claim 7, wherein said tangible medium is a visual display screen.

13. A non-transitory electronic-processor-readable medium having a plurality of electronic processor executable instructions stored thereon that, when executed by an electronic processor, causes the electronic processor to perform a method of determining sensitivity of at least one energetic composition material to explosive shock using an energetic determination tool to simulate an actual shape of a cumulative distribution function (CDF) for said at least one energetic composition material, comprising:

providing a grouping of sensitivity tests at particularized segments and patterned sensitivity test data associated with said grouping of sensitivity tests data, said grouping of sensitivity tests at particularized segments and said patterned sensitivity test data configured for input to at least one electronic processor;

providing historical pelletized explosive test data for said at least one energetic composition material, said historical pelletized explosive test data corresponding to previous tests performed on said at least one energetic composition material, said historical pelletized explosive test data configured for input to said at least one electronic processor;

providing an energetic determination tool associated with said at least one electronic processor, wherein said energetic determination tool is configured to determine the actual shape of a cumulative distribution function (CDF);

inputting patterned sensitivity test data into at least one electronic processor;

inputting historical pelletized explosive test data into at least one electronic processor;

determining a range of sensitivity values of said at least one energetic composition material based on said historical pelletized explosive test data, wherein said range is bounded by sensitivity endpoints;

dividing said range of sensitivity values into at least three segments between said sensitivity endpoints, said at least three segments corresponding to predetermined sensitivity levels based on said historical pelletized explosive data;

simulating sensitivity tests at each of said at least three segments, said sensitivity tests producing sensitivity test data;

recording said sensitivity test data and storing said sensitivity test data;

electronically determining a CDF by analyzing said sensitivity test data, wherein said analysis provides response data points, said response data points corresponding to a proportion of detonation events at said simulated sensitivity tests at each of said at least three segments;

electronically fitting a best fit curve through said response data points, wherein said best fit curve is defined as the actual shape of said CDF;

outputting said best fit curve in a tangible medium; and obtaining said at least one energetic composition material corresponding to the actual shape of said CDF.

14. The non-transitory electronic-processor-readable medium according to claim 13, said analyzing said simulated test data, further comprising:

stacking response data with a corresponding stimulus level for each response entry, wherein said response data are said response data points corresponding to said proportion of detonation events, wherein said stimulus level is energy applied to said at least one energetic composition material;

converting said proportion of detonation events at each of said corresponding stimulus level to a percentage;

identifying a probability distribution that best describes said response data points;

determining a probabilistic model for said fitting a best fit curve task, said determination based on said historical pelletized explosive data; and performing a probit analysis of said identified probability distribution that best describes said response data points.

15. The non-transitory electronic-processor-readable medium according to claim 13, wherein said outputting of said best fit curve further comprising visually displaying a fitted percent probability versus stimulus level, stimulus levels relative to the fitted probability, and the confidence intervals associated with the fitted probability.

16. The non-transitory electronic-processor-readable medium according to claim 13, wherein said at least three segments is three segments.

17. The non-transitory electronic-processor-readable medium according to claim 13, wherein said at least three segments is four segments.

18. The non-transitory electronic-processor-readable medium according to claim 13, wherein said tangible medium is a visual display screen.

* * * * *